(12) United States Patent
McCleskey et al.

(10) Patent No.: US 6,742,521 B2
(45) Date of Patent: Jun. 1, 2004

(54) COMBINATION PROPHYLACTIC AND SANITIZER

(76) Inventors: Larry McCleskey, 4570 Northside Dr. NW., Atlanta, GA (US) 30327; Andrew Cox, 2141 River Refuge Blvd., Blairsville, GA (US) 30512

( * ) Notice: Subject to any disclaimer, the term of this patent is extended or adjusted under 35 U.S.C. 154(b) by 0 days.

(21) Appl. No.: 10/165,230

(22) Filed: Jun. 7, 2002

(65) Prior Publication Data

US 2003/0226567 A1 Dec. 11, 2003

(51) Int. Cl.[7] .................................................. A61F 6/02
(52) U.S. Cl. ........................ 128/842; 128/844; 128/918; 206/69
(58) Field of Search ................................ 128/842, 844, 128/918; 604/347–353; 206/69

(56) References Cited

U.S. PATENT DOCUMENTS

| | | |
|---|---|---|
| 4,892,188 A | 1/1990 | Meadows |
| 4,925,033 A | 5/1990 | Stoner |
| 5,244,096 A | 9/1993 | Stoner |
| 6,257,400 B1 | 7/2001 | Woodhouse |

*Primary Examiner*—Michael A. Brown
(74) *Attorney, Agent, or Firm*—Myers & Kaplan, LLC; Joel D. Myers; Ashish D. Patel (57) ABSTRACT

A combination prophylactic and sanitizer that provides an expeditious, convenient and portable application for the hygienic, thorough, and effective cleaning and/or sanitization of one's genitalia prior to utilization of a condom and/or prior to and/or after any sexual contact, thus reducing and/or destroying any organic matter that may contribute to the proliferation of bacteria and disease.

18 Claims, 7 Drawing Sheets

COMBINATION PROPHYLACTIC AND SANITIZER

TECHNICAL FIELD

The present invention relates generally to prophylactics, and more specifically to a combination prophylactic and sanitizer. The present invention is particularly suitable for, although not strictly limited to, thoroughly and effectively cleaning and/or sanitizing one's genitalia prior to application of a prophylactic and/or after sexual intercourse.

BACKGROUND OF THE INVENTION

Prophylactics, more commonly known as condoms, are typically utilized to reduce the risk of pregnancy and the spread of sexually transmitted diseases, including the human immunodeficiency virus (HIV), which causes AIDS. As such, sexually active individuals will usually carry on their person conventional and readily available individually packaged condoms.

Although the standard packaged condom is convenient and portable, its fails to provide an individual with a means to clean and/or sanitize his/her genitalia prior to application of the condom and/or after sexual intercourse or contact when the condom is removed.

Furthermore, many sexual partners choose to engage in other sexual acts prior to actual sexual intercourse and prior to application of a condom. An individual engaging in such activity may wish to cleanse his/her own genitalia and/or his/her partner's genitalia without having to first shower or bath. Accordingly, many individuals may be hesitant to engage in such sexual activity if such sanitization is not readily accessible.

Therefore, it is readily apparent that there is a need for a combination prophylactic and sanitizer that provides an expeditious and convenient means of cleaning and/or disinfecting one's genitalia prior to application of a condom and/or prior to and/or after sexual activity.

BRIEF SUMMARY OF THE INVENTION

Briefly described, in a preferred embodiment, the present invention overcomes the above-mentioned disadvantages and meets the recognized need for such a device by providing a combination prophylactic and sanitizer that provides an expeditious, convenient and portable application for the hygienic, thorough, and effective cleaning and/or sanitization of one's genitalia prior to utilization of a condom and/or prior to and/or after any sexual contact, thus reducing and/or destroying any organic matter that may contribute to the proliferation of bacteria and disease.

According to its major aspects and broadly stated, the present invention in its preferred form is a combination prophylactic and sanitizer preferably having a prophylactic and a disinfecting/sanitization towelette or the like.

More specifically, the present invention is a combination prophylactic and sanitizer preferably having a prophylactic enclosed within a first package and a disinfecting/sanitization towelette, napkin, wipe, swab or the like enclosed within a second package, wherein the first and second packages are preferably attached together and separable from one another via perforations or the like, and wherein the first and second package are preferably of the size and type that enclose conventional individual condoms, thus reducing bulkiness and facilitating and maintaining convenient portability of the combination prophylactic and sanitizer.

A feature and advantage of the present invention is its ability to expeditiously and conveniently provide an individual with a means to thoroughly and effectively clean and/or sanitize his/her genitalia prior to utilization of a condom and/or prior to and/or after any sexual contact.

A feature and advantage of the present invention is its ability to reduce and/or destroy any organic matter that may contribute to the proliferation of bacteria and disease.

A feature and advantage of the present invention is its ability to maintain sterility until desired use.

A feature and advantage of the present invention is its portability.

A feature and advantage of the present invention is its compactness, thus facilitating its overall portability and/or discrete transport.

A feature and advantage of the present invention is its ease of use and application.

A feature and advantage of the present invention is its simplicity of design.

A feature and advantage of the present invention is its ease of storage.

A feature and advantage of the present invention is its ability to be adapted and/or altered to accommodate any size and/or type of condom and/or sanitizer.

A feature and advantage of the present invention is its ability to be adapted and/or altered to accommodate sexual lubricants, spermicidal solutions, cleansing solutions and/or antibacterial solutions.

A feature and advantage of the present invention is its ability to be adapted and/or altered to accompany separately sold and individually packaged condoms.

These and other objects, features and advantages of the present invention will become more apparent to one skilled in the art from the following description and claims when read in light of the accompanying drawings.

BRIEF DESCRIPTION OF THE DRAWINGS

The present invention will be better understood by reading the Detailed Description of the Preferred and Alternate Embodiments with reference to the accompanying drawing figures, in which like reference numerals denote similar structures and refer to like elements throughout, and in which.

DETAILED DESCRIPTION OF THE PREFERRED AND ALTERNATIVE EMBODIMENTS

In describing the preferred and alternate embodiments of the present invention, as illustrated in FIGS. 1–7, specific terminology is employed for the sake of clarity. The invention, however, is not intended to be limited to the specific terminology so selected, and it is to be understood that each specific element includes all technical equivalents that operate in a similar manner to accomplish similar functions.

Figure 1:
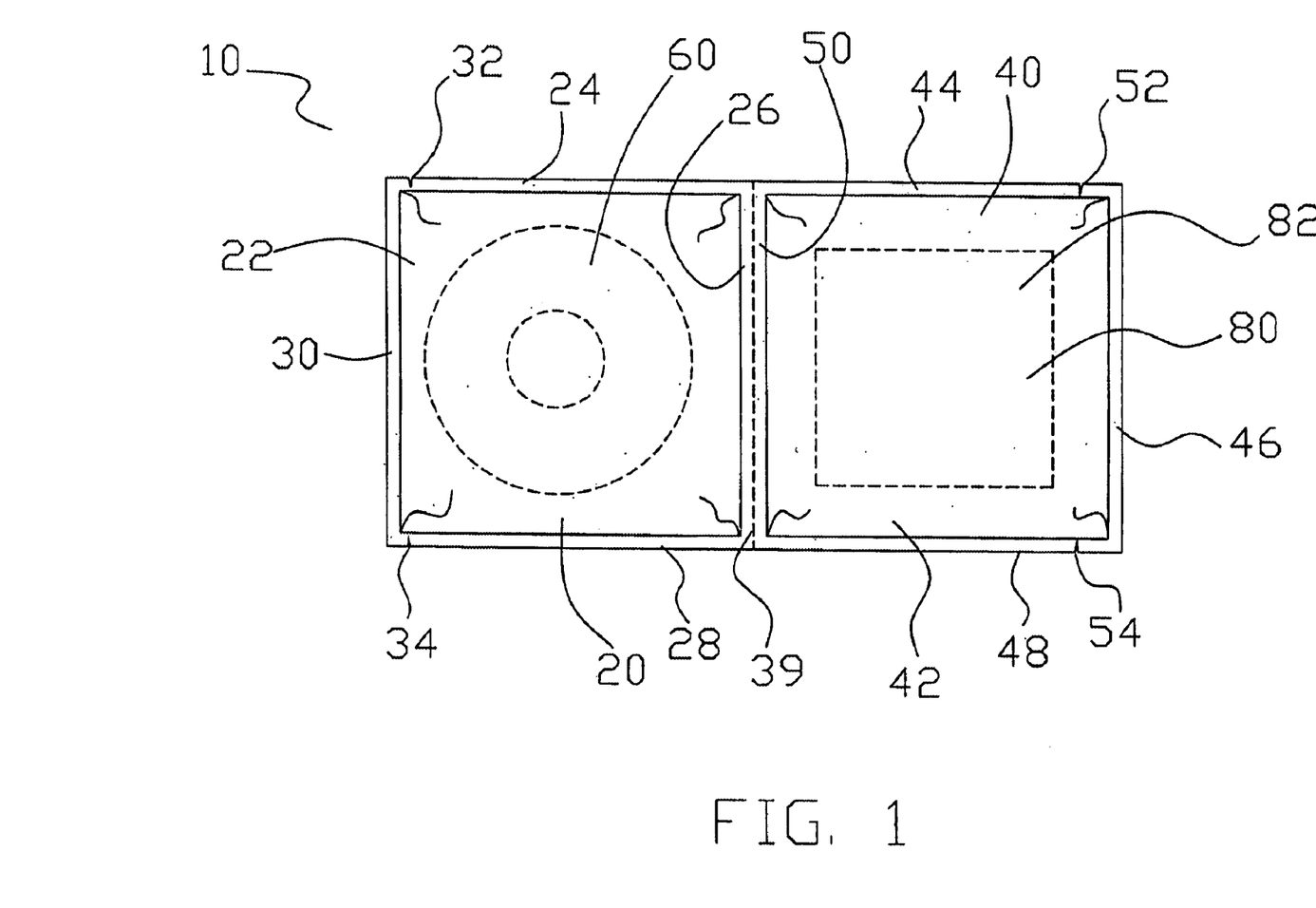
FIG. 1 is a top view of a combination prophylactic and sanitizer according to a preferred embodiment of the present invention.

Referring now to FIG. 1, the present invention in its preferred embodiment is a device 10, wherein device 10 is a combination prophylactic and sanitizer, generally having first package 20, second package 40, prophylactic 60 and sanitizer 80.

Specifically, first package 20 of device 10 is preferably substantially square-shaped and possesses a size equivalent to that of conventional individual male-condom packages, wherein first package 20 is formed from any suitable condom packaging known within the art, such as, for exemplary purposes only, heat sealable laminated films of aluminum foil, plastics and/or paper. Although the preferred size and shape of first package 20 is equivalent to that of conventional individual male-condom packages, it is contemplated in an alternate embodiment that first package 20 could possess any size and shape to facilitate accommodation of prophylactics such as, for exemplary purposes, female condoms and/or dental dam.

First package 20 preferably defines compartment 22, wherein compartment 22 is preferably dimensioned to contain prophylactic 60 therein, and wherein edges 24, 26, 28 and 30 of first package 20 are preferably sealed via any sealing means known within the art, such as, for exemplary purposes only, heat and/or hermetic sealing, so as to maintain sterility of enclosed prophylactic 60. Formed preferably on edges 24 and 26, proximal to edge 30, of first package 20 are slits 32 and 34, respectively, wherein slits 32 and 34 preferably enable a user of device 10 to tear open first package 20 and remove prophylactic 60 from compartment 22.

Preferably removably attached to edge 26 of first package 20 is second package 40, wherein first package 20 and second package 40 are preferably separable from one another via perforations 39 formed between edges 26 and 50 of first package 20 and second package 40, respectively; although other suitable means of separation may be utilized. Alternatively, first package 20 and second package 40 may be permanently affixed to one another at edges 26 and 50, respectively, and/or integrally formed with one another via heat sealing or the like as known with the art. As more fully described below, second package 40 preferably functions to contain sanitizer 80 therein.

Similar to first package 20 of device 10, second package 40 is preferably substantially square-shaped and preferably possesses a size approximate that of first package 20 and/or conventional individual male-condom packages, wherein second package 40 is formed from any suitable packaging material known within the art, such as, for exemplary purposes only, heat sealable laminated films of aluminum foil, plastics and/or paper. Although the preferred size and shape of second package 40 is equivalent to that of first package 20 and/or conventional individual male-condom packages, it is contemplated in an alternate embodiment that second package 40 could possess any size and shape to facilitate accommodation of any size, type and form of sanitizer 80.

Second package 40 preferably defines compartment 42, wherein compartment 42 is preferably dimensioned to contain sanitizer 80 therein, and wherein edges 44, 46, 48 and 50 of second package 40 are preferably sealed via any sealing means known within the art, such as, for exemplary purposes only, heat and/or hermetic sealing, so as to maintain sterility of enclosed sanitizer 80. Formed preferably on edges 44 and 46, proximal to edge 46, of second package 40 are slits 52 and 54, respectively, wherein slits 52 and 54 preferably enable a user of device 10 to tear open second package 40 and remove sanitizer 80 from compartment 42.

Although prophylactic 60 of first package 20 is preferably a conventional male condom, prophylactic 60 can be any available prophylactic such as, for exemplary purposes only, female condoms and/or dental dams, and can be formed from any conventional condom material such as, for exemplary purposes only, latex, polyurethane, natural membranes such as sheep skin, and/or any other synthetic polymers and/or hydrocarbons.

Sanitizer 80 is preferably a disposable towelette 82 or any other suitable napkin, wipe and/or swab dimensioned to foldably fit within compartment 42 of second package 40, wherein towelette 82 can be formed from any suitable material, such as, for exemplary purposes only, gauze, cotton, nylon, paper and/or any suitable combination thereof. To facilitate in the disinfecting and/or sanitization of the genitalia of a user of device 10, towelette 82 is preferably pre-moistened with a sterilizing agent such as, for exemplary purposes only, iodine solution, isopropyl alcohol and/or other alcohols suitable for use on scrotal tissue, germicidal solutions/gels, anitmicrobial solutions/gels, antibacterial solutions/gels, peroxide solutions/gels, antiseptic solutions/gels and/or any combination thereof. Additionally, towelette 82 may also contain lubricants and/or spermicidal such as nonoxynol-9. Although sanitizer 80 is preferably a towelette 82, it is contemplated in an alternate embodiment that sanitizer 80 could be a liquid/gel sterilizing agent alone.

Figure 2:
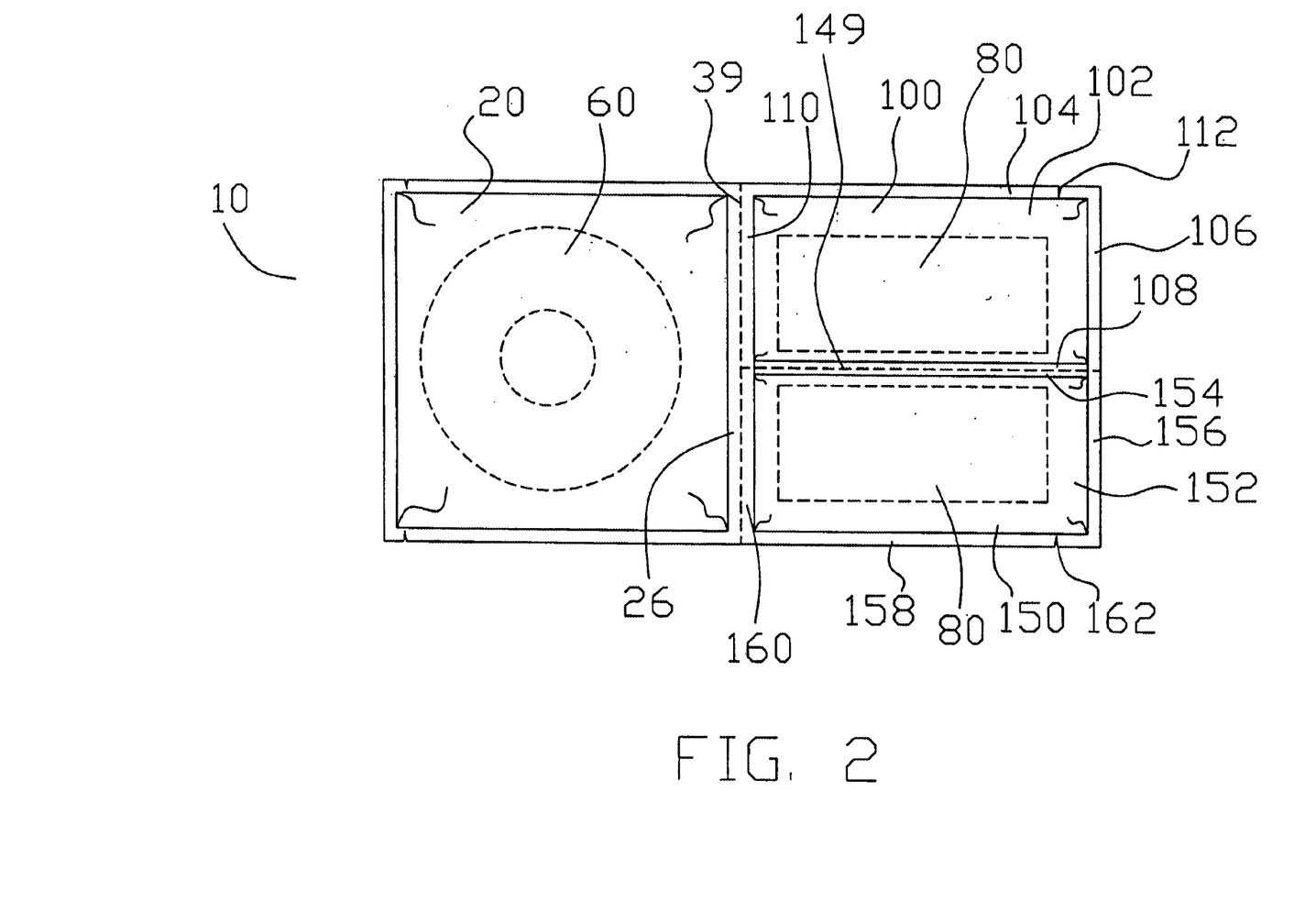
FIG. 2 is a top view of a combination prophylactic and sanitizer according to an alternate embodiment of the present invention.

Referring now to FIG. 2, in an alternate embodiment of device 10, removably attached to edge 26 of first package 20 is second package 100 and third package 150, wherein first package 20 is separable from second package 100 and third package 150 via perforations 39 formed between edges 26 of first package 20 and edges 110 and 160 of second package 100 and third package 150, respectively; although other suitable means of separation may be utilized. Second package 100 and third package 150 are separable from one another via perforations 149 formed between edges 108 and 154 of second package 100 and third package 150, respectively; although other suitable means of separation may be utilized. Alternatively, first package 20, second package 100 and third package 150, may be permanently affixed to one another at their respective edges and/or integrally formed with one another via heat sealing or the like as known with the art. As more fully described below, second package 100 and third package 150 function to contain sanitizers 80 therein. It is contemplated in an alternate embodiment that any number of packages containing sanitizers 80 therein could be attached to first package 20.

Second package 100 is preferably substantially rectangular-shaped and possesses a size equivalent to half of that of first package 20 and/or conventional individual male-condom packages, wherein second package 100 is formed from any suitable packaging material known within the art, such as, for exemplary purposes only, heat sealable laminated films of aluminum foil, plastics and/or paper. Although the preferred size and shape of second package 100 is equivalent to half of that of first package 20 and/or conventional individual male-condom packages, it is contemplated in an alternate embodiment that second package 100 could possess any size and shape to facilitate accommodation of any size, type and form of sanitizer 80 as disclosed above.

Second package 100 preferably defines compartment 102, wherein compartment 102 is preferably dimensioned to contain sanitizer 80 therein, and wherein edges 104, 106, 108 and 110 of second package 100 are preferably sealed via any sealing means known within the art, such as, for exemplary purposes only, heat and/or hermetic sealing, so as to maintain sterility of enclosed sanitizer 80. Formed preferably on edge 104 proximal to edge 106, of second package 100 is slit 112, wherein slit 112 preferably enables a user of device 10 to tear open second package 100 and remove sanitizer 80 from compartment 102.

Similar to second package 100, third package 150 is preferably substantially rectangular-shaped and possesses a size equivalent to half of that of first package 20 and/or conventional individual male-condom packages, wherein third package 150 is formed from any suitable packaging material known within the art, such as, for exemplary purposes only, heat sealable laminated films of aluminum foil, plastics and/or paper. Although the preferred size and shape of third package 150 is equivalent to half of that of first package 20 and/or conventional individual male-condom packages, it is contemplated in an alternate embodiment that third package 150 could possess any size and shape to facilitate accommodation of any size, type and form of sanitizer 80 as disclosed above.

Third package 150 preferably defines compartment 152, wherein compartment 152 is preferably dimensioned to contain sanitizer 80 therein, and wherein edges 154, 156, 158 and 160 of third package 150 are preferably sealed via any sealing means known within the art, such as, for exemplary purposes only, heat and/or hermetic sealing, so as to maintain sterility of enclosed sanitizer 80. Formed preferably on edge 158 proximal to edge 156, of third package 150 is slit 162, wherein slit 162 preferably enables a user of device 10 to tear open third package 150 and remove sanitizer 80 from compartment 152.

Second package 100 and third package 150 preferably each contain sanitizers 80 as disclosed above, wherein second package 100 could contain towelette 82 as disclosed above, and third package 150 could also contain towelette 82 as disclosed above or alternatively a liquid/gel sterilizing agent alone.

Figure 3:
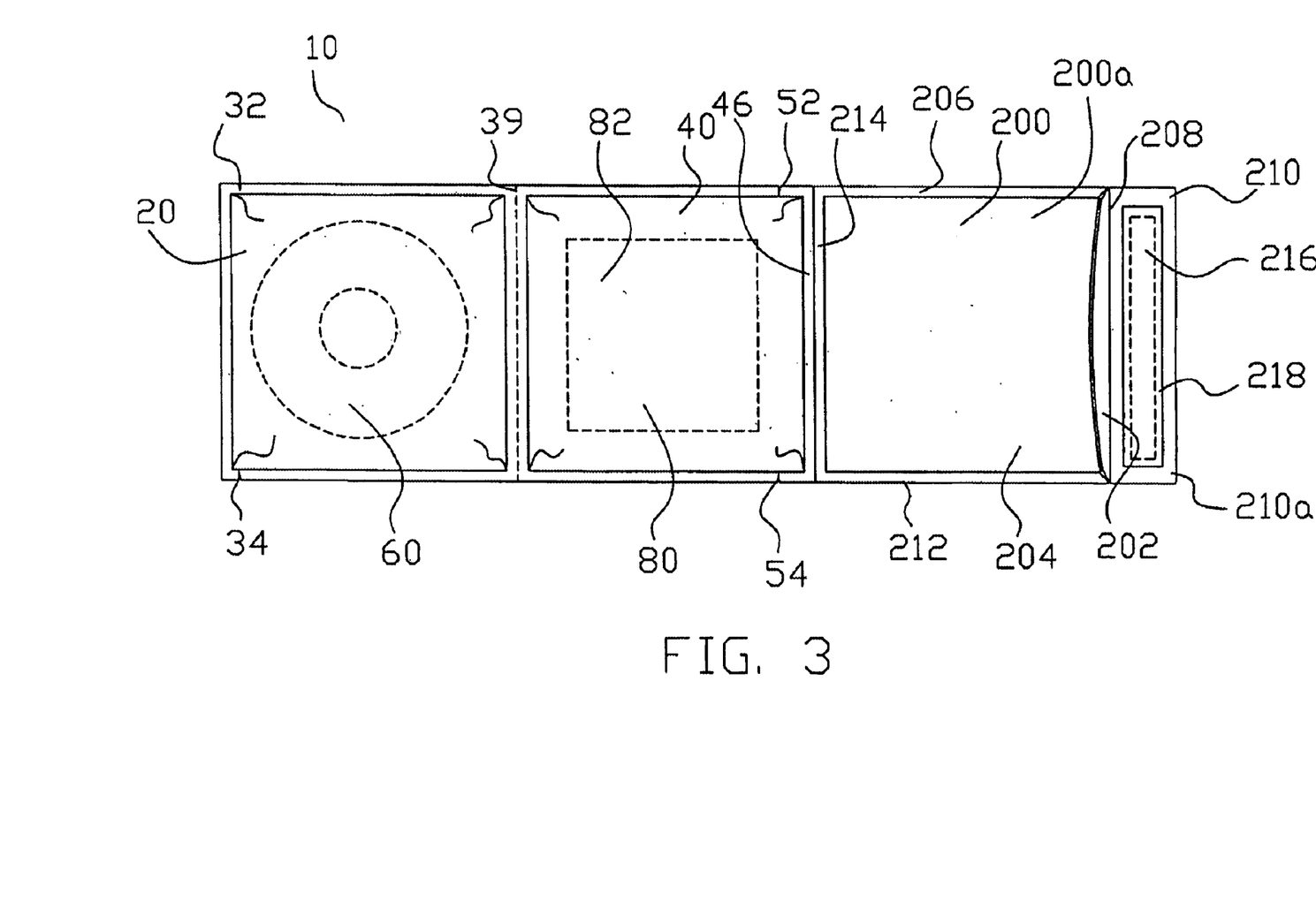
FIG. 3 is a top view of a combination prophylactic and sanitizer according to an alternate embodiment of the present invention.

Referring now to FIG. 3, in an alternate embodiment of device 10, attached to edge 46 of second package 40 is edge 214 of receptacle 200. Receptacle 200 is preferably substantially square-shaped and possesses a size equivalent to that of first package 20, second package 40, and/or conventional individual male-condom packages, wherein receptacle 200 is formed from any suitable packaging material known within the art, such as, for exemplary purposes only, heat sealable laminated films of aluminum foil, plastics and/or paper. Although the preferred size and shape of receptacle 200 is equivalent to that of first package 20, second package 40 and/or conventional individual male-condom packages, it is contemplated in an alternate embodiment that receptacle 200 could possess any size and shape to facilitate accommodation of soiled/used sanitizer 80 and/or contaminated/used prophylactic 60, as more fully described below.

Receptacle 200 preferably defines compartment 204, wherein compartment 204 is preferably dimensioned to receive and retain soiled/used towelette 82 of sanitizer 80 and/or prophylactic 60 therein, and wherein edges 206, 212 and 214 of receptacle 200 are preferably sealed via any sealing means known within the art, such as, for exemplary purposes only, heat and/or hermetic sealing. Compartment 204 is preferably accessible via aperture 202 formed preferably at edge 208 of receptacle 200. Formed preferably on edge 208 is sealing flap 210, wherein face 210a of sealing flap 210 preferably possesses an adhesive strip 216 formed thereon, and wherein adhesive strip 216 is exposable via removal of adhesive cover 218. As such, upon removal of towelette 82 from second package 40 via tearing along slits 52 and 54 of second package 40, and/or removal of prophylactic 60 from first package 20 via tearing along slits 32 and 34 of first package 20, and subsequent use of the same, soiled/used towelette 82 and/or prophylactic 60 can be placed within compartment 204 of receptacle 200 via aperture 202. Thereafter, adhesive cover 218 is removed from sealing flap 210 to expose adhesive strip 216, whereupon sealing flap 210, and ultimately adhesive strip 216, is brought into contact with surface 200a of receptacle 200, thus enclosing contaminated/used towelette 82 and/or prophylactic 60 within compartment 204 of receptacle 200.

Figure 4:
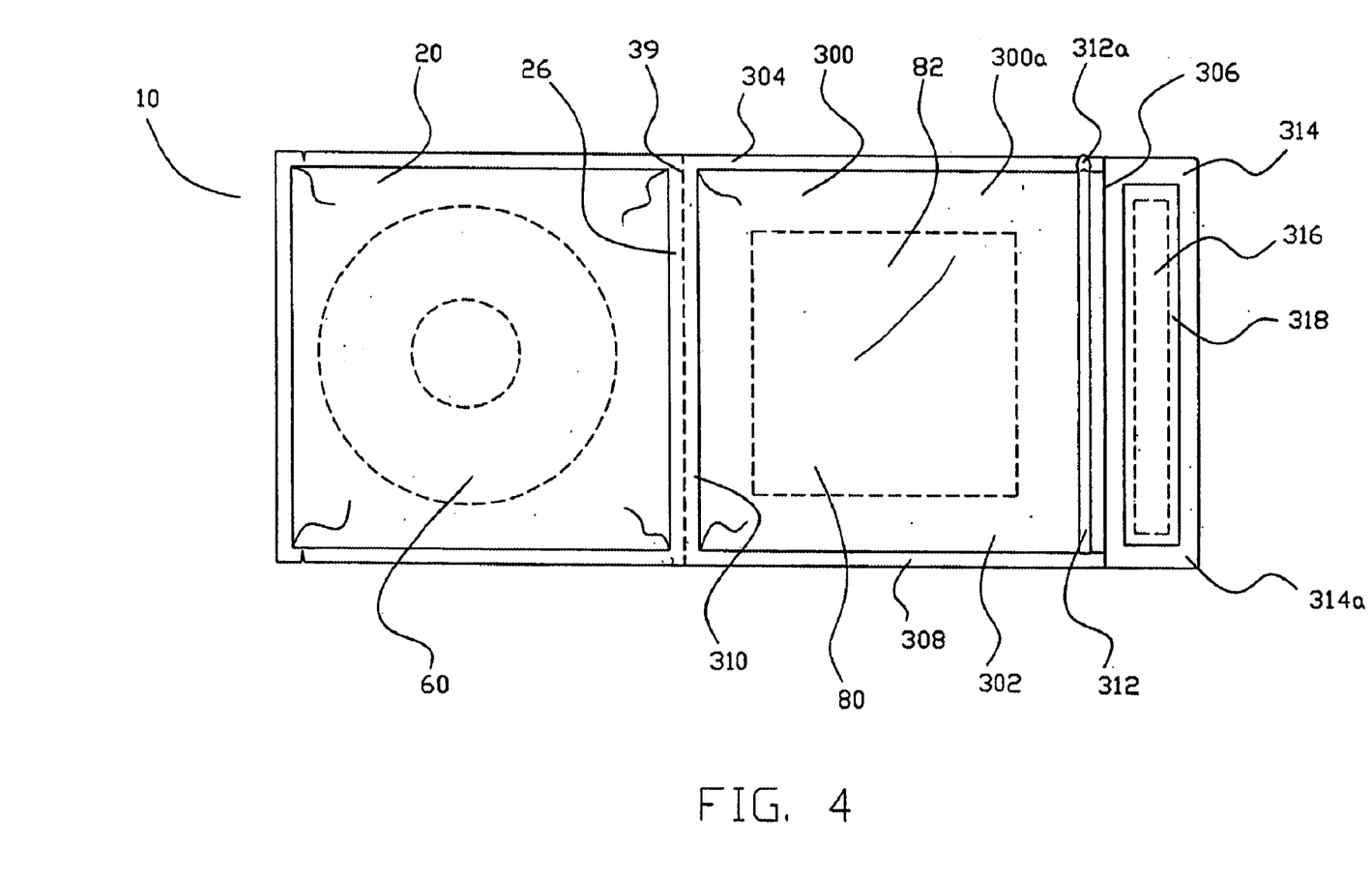
FIG. 4 is a top view of a combination prophylactic and sanitizer according to an alternate embodiment of the present invention.

Referring now to FIG. 4, in an alternate embodiment of device 10, preferably removably attached to edge 26 of first package 20 is edge 310 of second package 300, wherein first package 20 and second package 300 are preferably separable from one another via perforations 39 formed between edges 26 and 310 of first package 20 and second package 300, respectively; although other suitable means of separation may be utilized. Alternatively, first package 20 and second package 300 may be permanently affixed to one another at edges 26 and 310, respectively, and/or integrally formed with one another via heat sealing or the like as known with the art.

Second package 300 is preferably substantially square-shaped and possesses a size equivalent to that of first package 20 and/or conventional individual male-condom packages, wherein second package 300 is formed from any suitable packaging material known within the art, such as, for exemplary purposes only, heat sealable laminated films of aluminum foil, plastics and/or paper. Although the preferred size and shape of second package 300 is equivalent to that of first package 20 and/or conventional individual male-condom packages, it is contemplated in an alternate embodiment that second package 300 could possess any size and shape to facilitate accommodation of towelette 82 of sanitizer 80 and thereafter soiled/used towelette 82 and/or contaminated/used prophylactic 60, as more fully described below.

Second package 300 preferably defines compartment 302, wherein compartment 302 is preferably dimensioned to contain towelette 82 of sanitizer 80 and thereafter receive and retain soiled/used towelette 82 of sanitizer 80 and/or prophylactic 60, as more fully described below. Edges 304, 306, 308 and 310 of second package 300 are preferably sealed via any sealing means known within the art, such as, for exemplary purposes only, heat and/or hermetic sealing, so as to maintain sterility of enclosed sanitizer 80. Compartment 204 is preferably accessible via removal of tear strip 312, wherein tear strip 312 is preferably a thin plastic strip integrally formed with surface 300a of second package 300 and is preferably positioned proximal to edge 306 of second package 300. Tear strip 312 preferably possesses tab 312a, wherein downward movement/pulling of tab 312a preferably permits tear strip 312 to tear open surface 300a of second package 300, thus allowing access to compartment 302 and the enclosed sanitizer 80. Formed preferably on edge 306 is sealing flap 314, wherein face 314a of sealing flap 314 preferably possesses an adhesive strip 316 formed thereon, and wherein adhesive strip 316 is exposable via removal of adhesive cover 318. As such, upon removal of towelette 82 from second package 300 via pulling of tear strip 312, and subsequent use of the same, soiled/used towelette 82, and/or prophylactic 60, can be placed back into compartment 302 of second package 300. Thereafter, adhesive cover 318 is removed from sealing flap 314 to expose adhesive strip 316, whereupon sealing flap 314, and ultimately adhesive strip 316, is brought into contact with surface 300a of second package 300, thus enclosing contaminated/used towelette 82 and/or prophylactic 60 within compartment 302 of second package 300.

Figure 5:
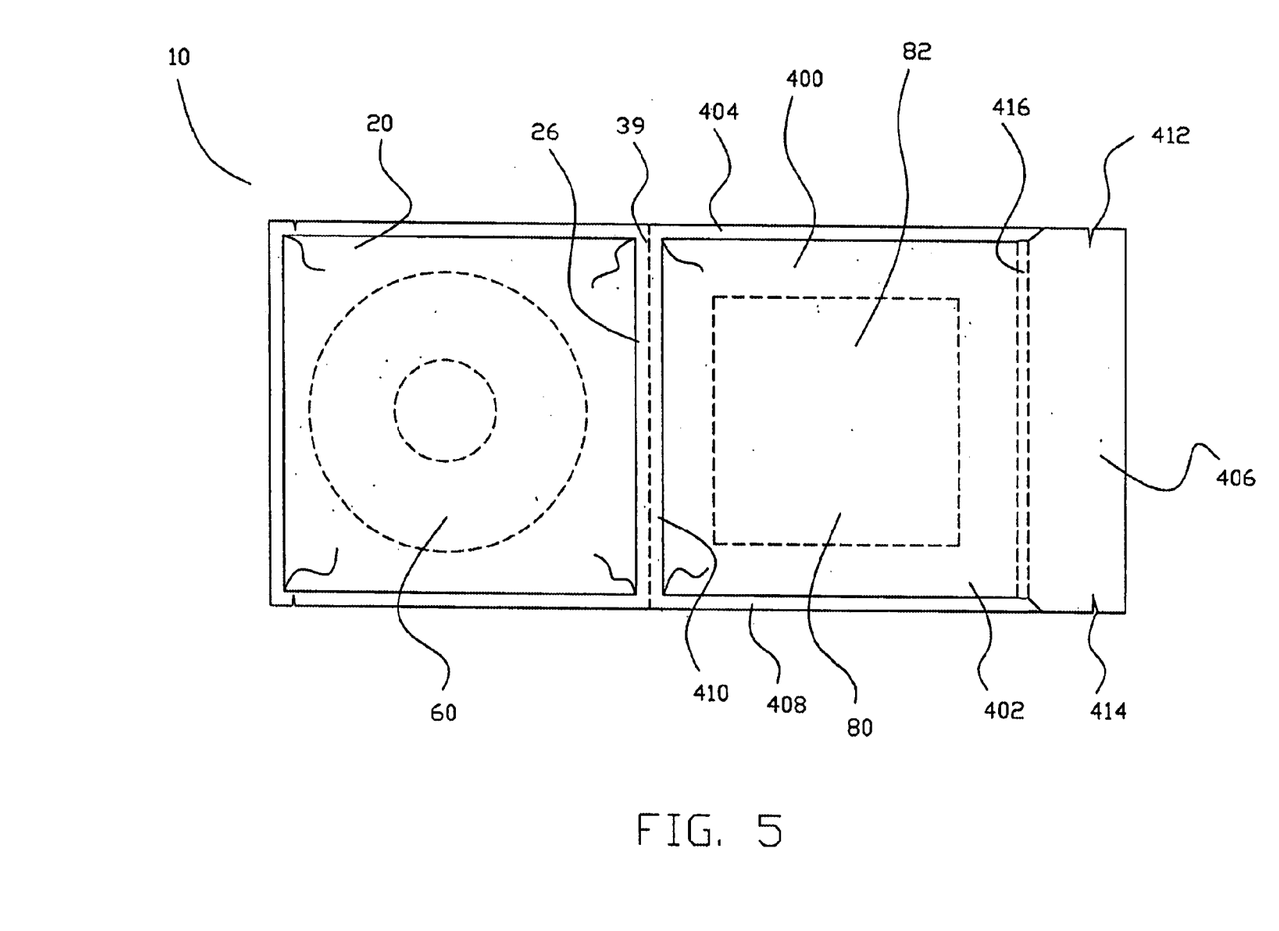
FIG. 5 is a top view of a combination prophylactic and sanitizer according to an alternate embodiment of the present invention.

Referring now to FIG. 5, in an alternate embodiment of device 10, preferably removably attached to edge 26 of first package 20 is edge 410 of second package 400, wherein first package 20 and second package 400 are preferably separable from one another via perforations 39 formed between edges 26 and 410 of first package 20 and second package 400, respectively; although other suitable means of separation may be utilized. Alternatively, first package 20 and second package 400 may be permanently affixed to one another at edges 26 and 410, respectively, and/or integrally formed with one another via heat sealing or the like as known with the art.

Second package 400 is preferably substantially square-shaped and possesses a size equivalent to that of first package 20 and/or conventional individual male-condom packages, wherein second package 400 is formed from any suitable packaging material known within the art, such as, for exemplary purposes only, heat sealable laminated films of aluminum foil, plastics and/or paper. Although the preferred size and shape of second package 400 is equivalent to that of first package 20 and/or conventional individual male-condom packages, it is contemplated in an alternate embodiment that second package 400 could possess any size and shape to facilitate accommodation of towelette 82 of sanitizer 80 and thereafter soiled/used towelette 82 and/or contaminated/used prophylactic 60, as more fully described below.

Second package 400 preferably defines compartment 402, wherein compartment 402 is preferably dimensioned to contain towelette 82 of sanitizer 80 and thereafter receive and retain soiled/used towelette 82 of sanitizer 80 and/or prophylactic 60, as more fully described below. Edges 404, 406, 408 and 410 of second package 400 are preferably sealed via any sealing means known within the art, such as, for exemplary purposes only, heat and/or hermetic sealing, so as to maintain sterility of enclosed sanitizer 80. Formed preferably on edges 404 and 408, proximal to edge 406, of second package 400 are slits 412 and 414, respectively, wherein slits 412 and 414 preferably enable a user of device 10 to tear open second package 400 and remove sanitizer 80 from compartment 402. After tearing along slits 412 and 414 of second package 400, compartment 402 is preferably accessible via separation of tongue-and-groove mechanism 416 formed preferably proximal to edge 406 of second package 400. As such, upon removal of towelette 82 from second package 400, and subsequent use of the same, soiled/used towelette 82, and/or prophylactic 60, can be placed back into compartment 402 of second package 400. Thereafter, tongue-and-groove mechanism 416 can be re-sealed, thus enclosing contaminated/used towelette 82 and/or prophylactic 60 within compartment 402 of second package 400.

Figure 6:
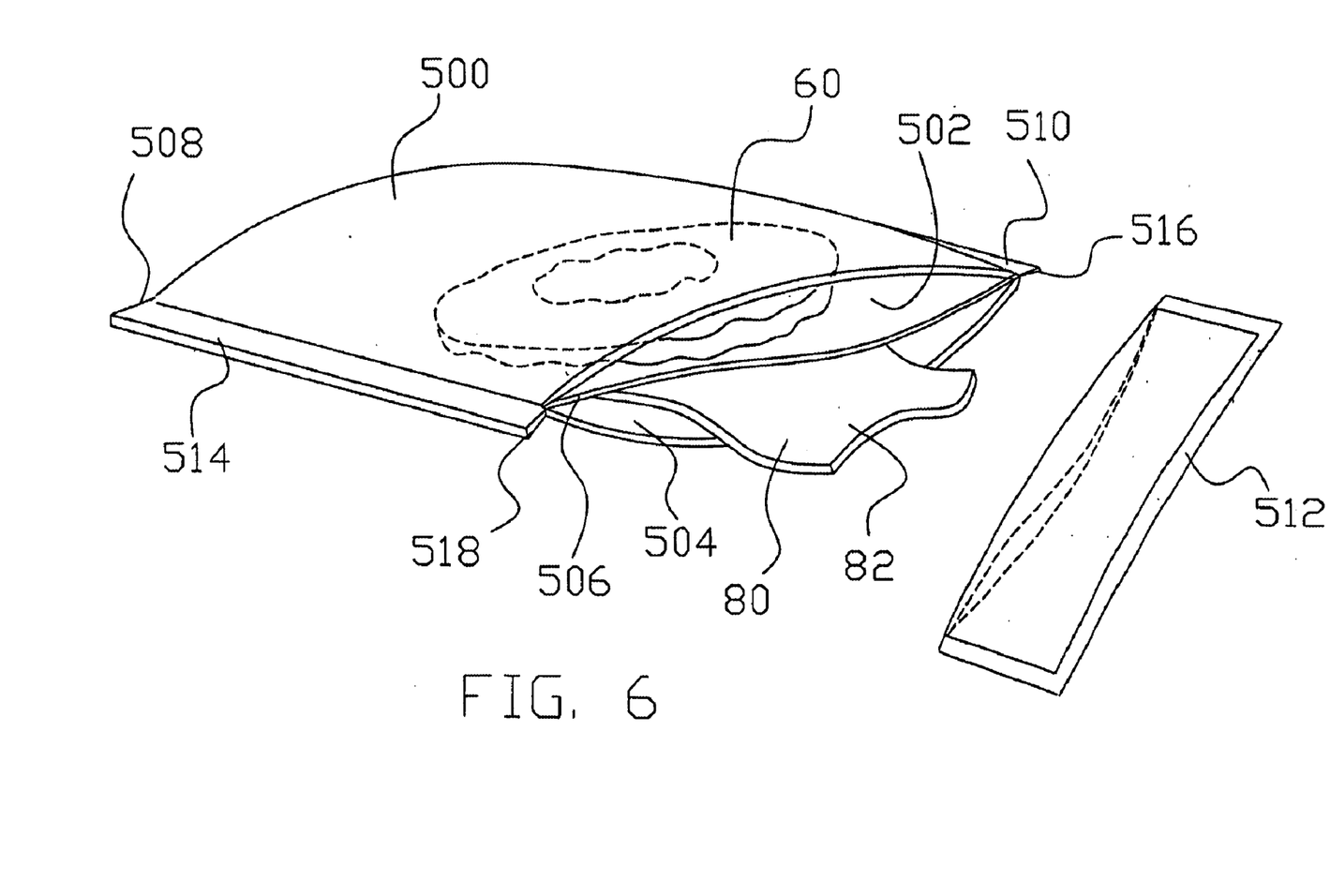
FIG. 6 is a perspective view of a combination prophylactic and sanitizer according to an alternate embodiment of the present invention.

Referring now to FIG. 6, in an alternate embodiment of device 10, package 500 is preferably substantially square-shaped and possesses a size equivalent to that of conventional individual male-condom packages, wherein package 500 is formed from any suitable packaging material known within the art, such as, for exemplary purposes only, heat sealable laminated films of aluminum foil, plastics and/or paper. Although the preferred size and shape of package 500 is equivalent to that of conventional individual male-condom packages, it is contemplated in an alternate embodiment that package 500 could possess any size and shape to facilitate accommodation of both sanitizer 80 and prophylactic 60, as more fully described below.

Package 500 is preferably bi-compartmental, having a divider 506 formed therein and preferably defining separate compartments 502 and 504, wherein compartments 502 and 504 are preferably dimensioned to contain prophylactic 60 and sanitizer 80, respectively. Edges 508, 510, 512 and 514 of package 500 are preferably sealed via any sealing means known within the art, such as, for exemplary purposes only, heat and/or hermetic sealing, so as to maintain sterility of enclosed sanitizer 80 and prophylactic 60. Formed preferably on edges 510 and 514, proximal to edge 512, of package 500 are slits 516 and 518, respectively, wherein slits 516 and 518 preferably enable a user of device 10 to tear open package 500 and remove prophylactic 60 from compartment 502 and sanitizer 80 from compartment 504 for subsequent use.

Figure 7:
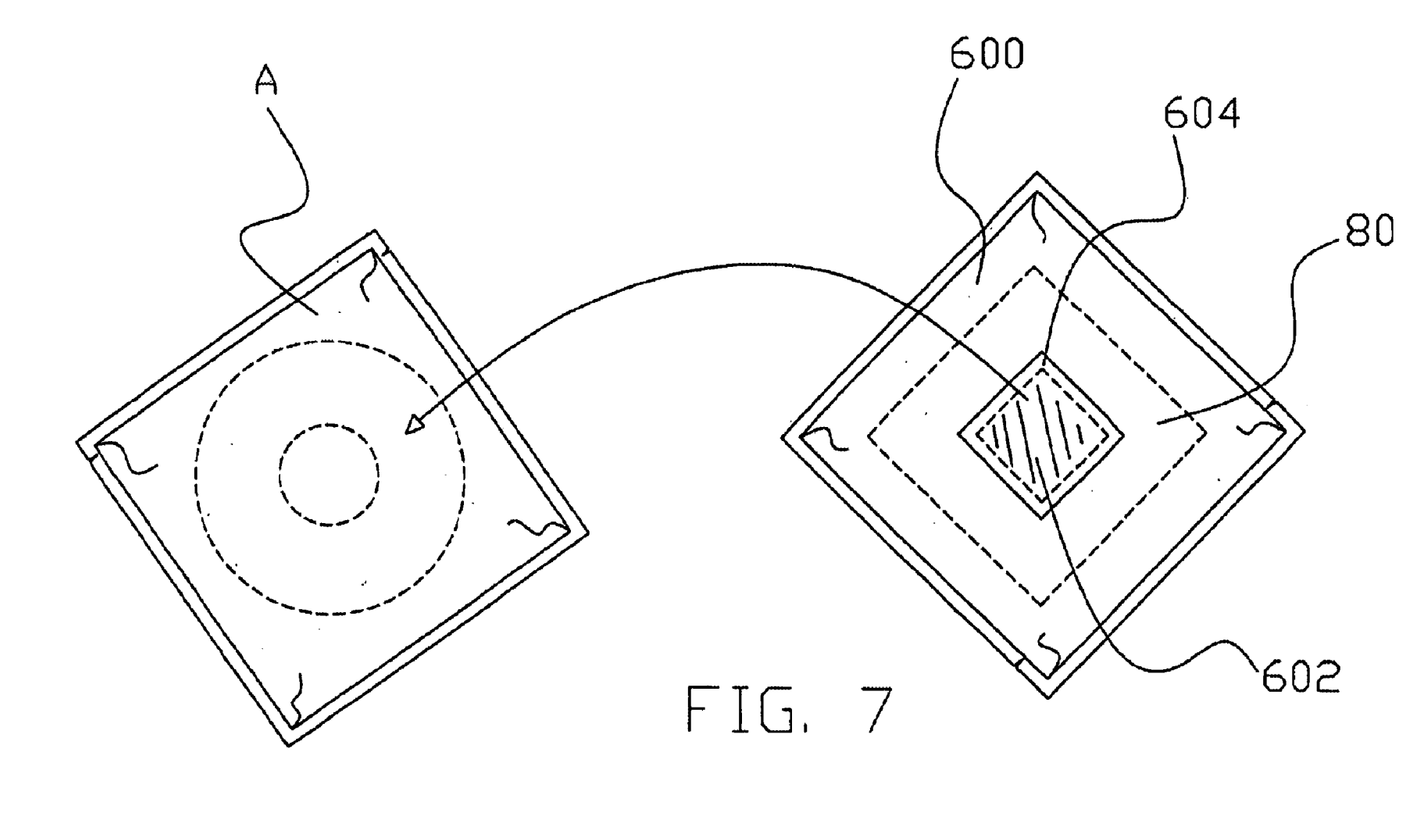
FIG. 7 is a perspective view of a combination prophylactic and sanitizer according to an alternate embodiment of the present invention.

Referring now to FIG. 7, it is contemplated in an alternate embodiment that package 600 having sanitizer 80 contained therein could be sold as a separate unit and attachable to a conventional packaged prophylactic A via adhesive strip 602 formed on package 600, wherein adhesive strip 602 preferably has adhesive cover 604 positioned thereon and removable therefrom prior to attachment.

It is contemplated in an alternate embodiment that device 10 could have any number of packages of prophylactics.

It is contemplated in an alternate embodiment that device 10 could have any number of packages of sanitizers.

It is contemplated in an alternate embodiment that device 10 could have any number of packages of prophylactics in combination with any number of packages of sanitizers.

It is contemplated in an alternate embodiment that device 10 could contain any type, size and form of sanitizer.

It is contemplated in an alternate embodiment that sanitizer 80 could be a sexually stimulating lubricant, cream, gel, oil, ointment and/or balm.

It is contemplated in an alternate embodiment that device 10 could contain any type, size and form of prophylactics.

It is contemplated in an alternate embodiment that device 10 could have any type, size and form of packages for containing the sanitizers.

It is contemplated in an alternate embodiment that device 10 could have any type, size and form of packages for containing the prophylactics.

Having thus described exemplary embodiments of the present invention, it should be noted by those skilled in the art that the within disclosures are exemplary only, and that various other alternatives, adaptations, and modifications may be made within the scope of the present invention. Accordingly, the present invention is not limited to the specific embodiments illustrated herein, but is limited only by the following claims.

What is claimed is:

1. A combination prophylactic and sanitizer, comprising:
   at least one first hermetically sealed disposable package containing at least one prophylactic; and
   at least one second hermetically sealed disposable package containing at least one sanitizer, wherein said at least one first package is associated with said at least one second package.

2. The combination prophylactic and sanitizer of claim 1, wherein said at least one first package and said at least one second packages are removably secured to one another.

3. The combination prophylactic and sanitizer of claim 1, further comprising at least one receptacle for receiving and retaining said at least one sanitizer and said at least one prophylactic, wherein said at least one receptacle comprises an adhesive-layered sealing flap for sealing said at least one sanitizer and said at least one prophylactic within said at least one receptacle.

4. The combination prophylactic and sanitizer of claim 2, further comprising a third package for housing a second at least one sanitizer.

5. The combination prophylactic and sanitizer of claim 1, wherein said at least one sanitizer is a towelette, said towelette being pre-moistened with an antiseptic.

6. The combination prophylactic and sanitizer of claim 1, wherein said at least one sanitizer is a napkin, said napkin being pre-moistened with an anti-bacterial solution.

7. The combination prophylactic and sanitizer of claim 1, wherein said at least one sanitizer is a liquid antiseptic.

8. The combination prophylactic and sanitizer of claim 1, wherein said at least one sanitizer is a liquid anti-bacterial.

9. A combination prophylactic and sanitizer, comprising:
   at least one prophylactic hermetically sealed within a disposable first package; and
   at least one sanitizer hermetically sealed within a disposable second package, wherein said first package and said second package are removably secured to one another.

10. The combination prophylactic and sanitizer of claim 9, further comprising at least one receptacle for receiving and retaining said at least one sanitizer and said at least one prophylactic, wherein said at least one receptacle comprises an adhesive-layered sealing flap for sealing said at least one sanitizer and said at least one prophylactic within said at least one receptacle.

11. The combination prophylactic and sanitizer of claim 9, further comprising a third package for housing a second at least one sanitizer.

12. The combination prophylactic and sanitizer of claim 9, wherein said at least one sanitizer is a towelette, said towelette being pre-moistened with an antiseptic.

13. The combination prophylactic and sanitizer of claim 9, wherein said at least one sanitizer is a napkin, said napkin being pre-moistened with an anti-bacterial solution.

14. The combination prophylactic and sanitizer of claim 9, wherein said at least one sanitizer is a liquid antiseptic.

15. The combination prophylactic and sanitizer of claim 9, wherein said at least one sanitizer is a liquid anti-bacterial.

16. A combination prophylactic and sanitizer, comprising:
   at least one prophylactic enclosed within a first package;
   at least one sanitizer enclosed within a second package, said second package being removable secured to said first package; and
   at least one receptacle for receiving and retaining said at least one sanitizer and said at least one prophylactic, wherein said at least one receptacle comprises an adhesive-layered sealing flap for sealing said at least one sanitizer and said at least one prophylactic within said at least one receptacle.

17. The combination prophylactic and sanitizer of claim 16, wherein said at least one sanitizer is a towelette, said towelette being pre-moistened with an antiseptic.

18. The combination prophylactic and sanitizer of claim 16, wherein said at least one sanitizer is a liquid antiseptic.

* * * * *